(12) United States Patent
Fritz et al.

(10) Patent No.: US 8,637,721 B2
(45) Date of Patent: Jan. 28, 2014

(54) CATALYST COMPOSITION AND PROCESS FOR DI-, TRI- AND/OR TETRAMERIZATION OF ETHYLENE

(75) Inventors: Peter M. Fritz, Unterhaching (DE); Heinz Bölt, Wolfratshausen (DE); Anina Wöhl, Pullach (DE); Wolfgang Müller, Munich (DE); Florian Winkler, Munich (DE); Anton Wellenhofer, Munich (DE); Uwe Rosenthal, Lambrechtshagen (DE); Bernd H. Müller, Rostock (DE); Marko Hapke, Rostock (DE); Normen Peulecke, Rostock (DE); Mohammed Hassan Al-Hazmi, Riyadh (SA); Vugar O. Aliyev, Riyadh (SA); Fuad Mohammed Mosa, Riyadh (SA)

(73) Assignees: Saudi Basic Industries Corporation, Riyadh (SA); Linde AG (DE)

( * ) Notice: Subject to any disclaimer, the term of this patent is extended or adjusted under 35 U.S.C. 154(b) by 673 days.

(21) Appl. No.: 12/452,594

(22) PCT Filed: Jun. 16, 2008

(86) PCT No.: PCT/EP2008/004815
§ 371 (c)(1),
(2), (4) Date: Apr. 5, 2010

(87) PCT Pub. No.: WO2009/006979
PCT Pub. Date: Jan. 15, 2009

(65) Prior Publication Data
US 2010/0190939 A1    Jul. 29, 2010

(30) Foreign Application Priority Data
Jul. 11, 2007   (EP) .................................. 07013543

(51) Int. Cl.
*C07C 2/22*   (2006.01)
*B01J 31/18*   (2006.01)

(52) U.S. Cl.
USPC .......... 585/513; 585/510; 585/511; 585/512; 585/520; 585/521; 585/522; 502/117; 502/118; 502/121; 502/123; 502/124

(58) Field of Classification Search
USPC ......... 502/102, 103, 118, 121, 123, 124, 117; 585/502, 510, 511, 512, 513, 520, 521, 585/522
See application file for complete search history.

(56) References Cited

U.S. PATENT DOCUMENTS

| | | | |
|---|---|---|---|
| 5,770,684 A * | 6/1998 | Stewart et al. | 528/392 |
| 5,968,866 A * | 10/1999 | Wu | 502/155 |
| 6,337,297 B1 * | 1/2002 | Mimura et al. | 502/117 |
| 6,800,702 B2 * | 10/2004 | Wass | 526/124.3 |
| 7,022,788 B2 * | 4/2006 | Wass | 526/172 |
| 2006/0173226 A1 | 8/2006 | Blann et al. | |

FOREIGN PATENT DOCUMENTS

| | | |
|---|---|---|
| WO | 9305389 A1 | 3/1993 |
| WO | WO9737765 A1 | 10/1997 |
| WO | WO0110876 A1 | 2/2001 |
| WO | WO0204119 A1 | 1/2002 |
| WO | 03053890 A1 | 7/2003 |
| WO | 2004056479 A1 | 7/2004 |
| WO | WO 2004056478 A1 * | 7/2004 |
| WO | 2005039758 A1 | 5/2005 |
| WO | WO2007057458 A1 | 5/2007 |

OTHER PUBLICATIONS

Steiner, et al., "From Neutral Iminophosphoranes to Multianionic Phosphazenates. The Coordination Chemistry of Imino-Aza-P(V) Ligands" in Coordination Chemistry Reviews, 227 (2002), 193-216—month unknown.*

Dixon, J.T. et al. "Advances in selectrive ethylene trimerisation—a critical overview", Journal of Organometallic Chemistry, Elsevier-Sequoia S.A. Lausanne, CH, vol. 689, No. 23 (Nov. 11, 2004), p. 3641-3668.

McGuiness, David S. et al., "Cocatalyst Influence in Selective Oligomerization: Effect on Activity, Catalyst Stability, and 1-Hexene/1-Octene Selectivity in the Ethylene Trimerization and Tetramerization Reaction", Organometallics, ACS, Washington, D.C., US, vol. 26, No. 10; (Apr. 10, 2007); p. 2561-2569.

Wrackmeyer, Bernd et al., "The first 1,3,2-diazaphospha-[3]ferrocenophanes", Inorganic Chemistry Communications, 7(7); (Jun. 8, 2004); p. 884-888.

Keat, R et al., "Preparation of bis-(N-alkyl-N-diphenylphosphinoamino)phenylphosphines and their reactions with sulphur and methyl iodide", Journal of the Chemical Society A., (1970); p. 2715-2719.

Burford, Neil et al., "Sequential dehydrochloride coupling of trichlorophosphine with 2,6-di-isopropylaniline: aminophosphine precursors to phosphetidines", Canadian Journal of Chemistry, 80(11), (Oct. 7, 2002), p. 1404-1409.

Scherer, Otto J, et al. "Synthesis and isolation of cis- and trans-1,3,2. lambda. 3,4.lambda.3-diazadiphosphetidine", Angewandte Chemie Int. Ed. Engl., vol. 15, No. 12, (1976), p. 772-772.

(Continued)

*Primary Examiner* — In Suk Bullock
*Assistant Examiner* — Bradley Etherton
(74) *Attorney, Agent, or Firm* — Cantor Colburn LLP

(57) ABSTRACT

The present invention relates to a catalyst composition and a process for di-, tri- and/or tetramerization of ethylene, wherein the catalyst composition comprises a chromium compound, a ligand of the general structure (A) $R_1R_2P$—$N(R_3)$—$P(R_4)$—$N(R_5)$—H or (B) $R_1R_2P$—$N(R_3)$—$P(R_4)$—$N(R_5)$—$PR_6R_7$, or any cyclic derivatives of (A) and (B), wherein at least one of the P or N atoms of the PNPN-unit or PNPNP-unit is member of a ring system, the ring system being formed from one or more constituent compounds of structures (A) or (B) by substitution and a co-catalyst or activator.

20 Claims, 1 Drawing Sheet

(56) References Cited

OTHER PUBLICATIONS

Katz, Stephanie A. et al., "Diastereoselectivity in the Formation of Skeletally Stabilized Phosphazanes", Inorganic Chemistry 33(9), (1994), p. 1762-9.

Helm, Monte L., et al., "Synthesis, Characterization, and Solution Properties of Skeletally Stabilized Triphosphazanes" Inorganic Chemistry, 38(13), (Jun. 8, 1999), p. 3167-3172.

Moskva, V.V. et al., "N,N'-Diphosphorylated 1,3,2-diazaphospholanes", Database CA [Online], Chemical Abstracts Service, Columbus, Ohio, US (I985).

Mundt, Cornelia et al., "N-Phosphanylated 1,3,2-oxaza- and 1,3,2-diazaphospholanes and phosphorinanes", Phosphorus, Sulfur and Silicon and the Related Elements, 88(1-4), (1994), p. 75-81.

Wannagat, U., et al., "Novel inorganic ring systems. XXIV. Attempts at preparation of phosphorus nitrogen-silicon containing ring systems", Zeitschrift Fuer Anorganische Und Allgemeine Chemie, 420(2), (1976), p. 119-31.

Gudat, Dietrich et al., "Synthesis structure and chemical reactivity of a stable pentamethylcyclopentadienyl-substituted phosphanylium ion: (pentamethycyplopentadienyl) (tert-butylamino) phosphanylium tetrachloroaluminate", Journal of the Chemical Society, Dalton Transactions: Inorganic Chemistry, 1972-1999; (1989), p. 693-700.

Scherer, Otto J. et al. "Synthesis and isolation of cis- and trans-1,3,2.lambda.3,4.lambda.3-diazadiphosphetidine", Angewandte Chemie Int. Ed. Engl., vol. 15, No. 12, (1976), p. 772-772.

Gudat, Dietrich et al., "Synthesis structure and chemical reactivity of a stable pentamethylcyclopentadienyl-substituted phosphanylium ion: (pentamethycyclopentadienyl) (tert-butylamino) phosphanylium tetrachloroaluminate", Journal of the Chemical Society, Dalton Transactions: Inorganic Chemistry, 1972-1999; (1989), p. 693-700.

International Search Report; International Application No. PCT/EP2008/004815; International Filing Date: Jun. 16, 2008; Date of Mailing: Feb. 9, 2009; 7 Pages.

Written Opinion of the International Searching Authority; International Application No. PCT/EP2008/004815; International Filing Date: Jun. 16, 2008; Date of Mailing: Feb. 9, 2009; 9 Pages.

* cited by examiner

GC/FID analysis of the liquid phase. Experimental conditions according to example 2.
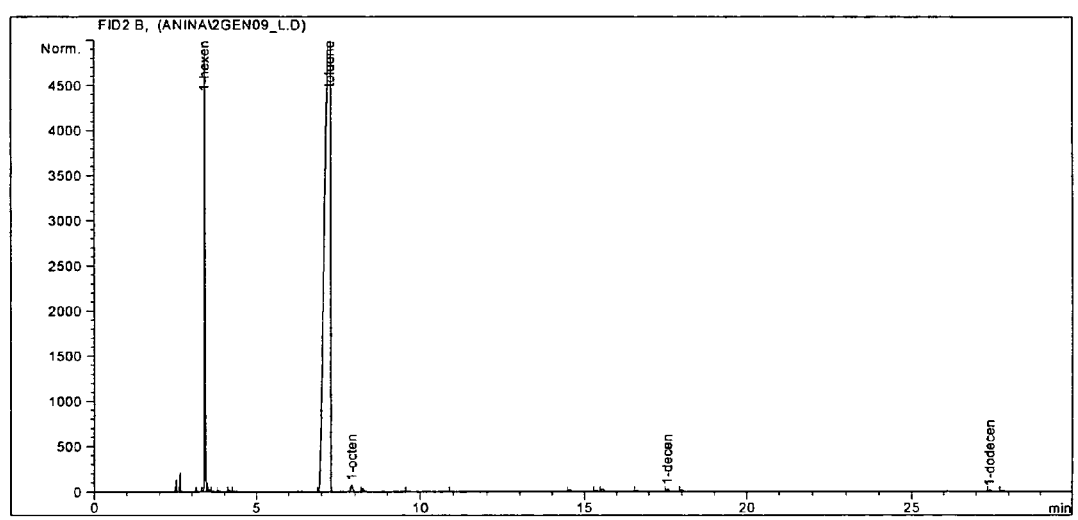

CATALYST COMPOSITION AND PROCESS FOR DI-, TRI- AND/OR TETRAMERIZATION OF ETHYLENE

The present invention relates to a catalyst composition and a process for the di-, tri- and/or tetramerization of ethylene.

Existing processes for the production of linear alpha olefins (LAOs), including comonomer-grade 1-hexene and 1-octene, rely on the oligomerization of ethylene. These processes have in common that they lead to a product distribution of ethylene-oligomers of chain length 4, 6, 8 and so on. This is due to a chemical mechanism which is widely governed by competing chain growth- and displacement reaction steps, leading to a Schulz-Flory- or Poisson-product distribution.

From the marketing point of view, this product distribution poses a formidable challenge for the full-range alpha olefins producer. The reason is that each market segment served exhibits a very different behavior in terms of market size and growth, geography, fragmentation etc. It is, therefore, very difficult for the producer to adapt to the market requirements since part of the product spectrum might be in high demand in a given economic context, while at the same time other product cuts might not be marketable at all or only in a marginal niche. Currently, the highest-value LAO product is comonomer-grade 1-hexene for the polymer industry, while 1-octene demand is also growing at a considerable rate.

Thus, the on-purpose production of the most economically viable LAOs, i.e. comonomer-grade 1-hexene and 1-octene, appears highly desirable. To meet the requirements regarding high C6- and/or C8-selectivities, new processes have been developed. The only known selective C6-commercial process has been commissioned by Chevron Phillips, see for a comprehensive review e.g. J. T. Dixon, M. J. Green, F. M. Hess, D. H. Morgan, "Advances in selective ethylene trimerisation—a critical overview", Journal of Organometallic Chemistry 689 (2004) 3641-3668.

Furthermore, patent applications have been filed by Sasol (WO 93/053891 A1), disclosing chromium-based selective ethylene-trimerization catalyst systems, typically of the type $CrCl_3$(bis-(2-diphenylphosphino-ethyl)amine)/MAO (methylaluminoxane). Also disclosed were variations of the ligand structure (e.g. bis(2-diethylphosphino-ethyl)-amine, pentamethyldiethylenetriamine etc.). However, all these complexes generate considerable amounts of unwanted side products such as LAOs other than 1-hexene and polyethylene.

A large body of scientific publications and patent literature describes the use of chromium-based metal-organic complexes with ligands featuring the basic PNP-structure (for example bis(diphenylphosphino)amine-ligands) (D. S. McGuinness, P. Wasserscheid, W. Keim, C. Hu, U. Englert, J. T. Dixon, C. Grove, "Novel Cr-PNP complexes as catalysts for the trimerization of ethylene", Chem. Commun., 2003, 334-335; K. Blann, A. Bollmann, J. T. Dixon, F. M. Hess, E. Killian, H. Maumela, D. H. Morgan, A. Neveling, S. Otto, M. J. Overett, "Highly selective chromium-based ethylene trimerisation catalysts with bulky diphosphinoamine ligands", Chem. Comm., 2005, 620-621; M. J. Overett, K. Blann, A. Bollmann, J. T. Dixon, F. Hess, E. Killian, H. Maumela, D. H. Morgan, A. Neveling, S. Otto, "Ethylene trimerisation and tetramerisation catalysts with polar-substituted diphosphinoamine ligands", Chem. Commun., 2005, 622-624; A. Jabri, P. Crewdson, S. Gambarotta, I. Korobkov, R. Duchateau, "Isolation of a Cationic Chromium(II) Species in a Catalytic System for Ethylene Tri- and Tetramerization", Organometallics 2006, 25, 715-718; T. Agapie, S. J. Schofer, J. A. Labinger, J. E. Bercaw, "Mechanistic Studies of the Ethylene Trimerization Reaction with Chromium-Diphosphine Catalysts: Experimental Evidence for a Mechanism Involving Metallacyclic Intermediates", J. Am. Chem. Soc. 2004, 126, 1304-1305; S. J. Schofer, M. D. Day, L. M. Henling, J. A. Labinger, J. E. Bercaw, "Ethylene Trimerization Catalysts Based on Chromium Complexes with a Nitrogen-Bridged Diphosphine Ligand Having ortho-Methoxyaryl or ortho-Thiomethoxy Substituents: Well-Defined Catalyst Precursors and Investigations of the Mechanism", Organometallics 2006, 25, 2743-2749; S. J. Schofer, M. D. Day, L. M. Henling, J. A. Labinger, J. E. Bercaw, "A Chromium-Diphosphine System for Catalytic Ethylene Trimerization: Synthetic and Structural Studies of Chromium Complexes with a Nitrogen-Bridged Diphosphine Ligand with ortho-Methoxyaryl Substituents", Organometallics 2006, 25, 2733-2742; P. R. Elowe, C. McCann, P. G. Pringle, S. K. Spitzmesser, J. E. Bercaw, "Nitrogen-Linked Diphosphine Ligands with Ethers Attached to Nitrogen for Chromium-Catalyzed Ethylene Tri- and Tetramerization", Organometallics 2006, 25, 5255-5260; WO 2004/056578, WO 2004/056479, EP 02 794 480.0, EP 02 794 479.2; or the SNS-structure (D. S. McGuinness, D. B. Brown, R. P. Tooze, F. M. Hess, J. T. Dixon, A. M. Z. Slavin, "Ethylene Trimerization with Cr-PNP and Cr-SNS Complexes: Effect of Ligand Structure, Metal Oxidation State, and Role of Activator on Catalysis", Organometallics 2006, 25, 3605-3610; A. Jabri, C. Temple, P. Crewdson, S. Gambarotta, I. Korobkov, R. Duchateau, "Role of the Metal Oxidation State in the SNS-Cr Catalyst for Ethylene Trimerization: Isolation of Di- and Trivalent Cationic Intermediates", J. Am. Chem. Soc. 2006, 128, 9238-9247; C. Temple, A. Jabri, P. Crewdson, S. Gambarotta, I. Korobkov, R. Duchateau, "The Question of the Cr-Oxidation State in the {Cr(SNS)} Catalyst for Selective Ethylene Trimerization: An Unanticipated Re-Oxidation Pathway", Angew. Chem. Int. Ed. 2006, 45, 7050-7053); for both, trimerization and tetramerization of ethylene. Excess amounts of MAO are most commonly used as activator/co-catalyst.

While the majority of the published studies rely on Cr-PNP complexes, some deal with other ligands, e.g. of the general formula (R1)(R2)P—X—P(R3)(R4), where X is a bivalent organic bridging group, see WO 2005/039758 A1, or deal with entirely different complexes, such as titanocenes (H. Hagen, W. P. Kretschmer, F. R. van Buren, B. Hessen, D. A. van Oeffelen, "Selective ethylene trimerization: A study into the mechanism and the reduction of PE formation", Journal of Molecular Catalysis A: Chemical 248 (2006) 237-247). In either case, the major concern is always selectivity and minimization of polyethylene formation.

The ethylene trimerization and tetramerization catalysts and processes disclosed so far in scientific and patent literature generally have one or more of the following disadvantages:

- Low selectivities to the desired products 1-hexene and/or 1-octene (undesired byproducts from side reaction channels).
- Limited purities of the products, i.e. the selectivities within the specific C6- or C8-cut (isomerization, branched olefin formation etc.).
- Wax formation, i.e. formation of heavy, long-chain, high carbon-number products.
- Polymer formation (polyethylene, branched and/or cross-linked PE); this leads to considerable product yield loss and fouling of equipment.
- Poor turnover rates/catalyst activity, resulting in high cost per kg product.
- High catalyst- or ligand cost.
- Difficult ligand synthesis, resulting in poor availability and high catalyst cost.

Susceptibility of catalyst performance, in terms of both activity and selectivity, to trace impurities (catalyst losses/-poisoning).

Difficult handling of catalyst components in a technical environment (catalyst complex synthesis, pre-mixing, inertization, catalyst- or ligand recovery).

Harsh reaction conditions, i.e. high temperatures and pressures, resulting in high invest-, maintenance-, and energy cost.

High co-catalyst/activator cost and/or consumption

Susceptibility to varying co-catalyst qualities; often the case when larger amounts of relatively ill-defined compounds must be used as activators (e.g. certain MAO-varieties).

It is an object of the present invention to provide a catalyst composition and a process for selective di-, tri- and/or tetramerization of ethylene overcoming the disadvantages of the prior art. Especially, higher selectivities shall be achieved with avoidance of formation of considerable amounts of waxes and polymers, regardless of the process conditions. Further, the catalyst composition shall also provide sufficiently high activity turnover frequency for a technical process.

In other words, the broad spectrum of LAO (linear alpha olefins) products in prior art processes shall be avoided and the selective production of preferably the economically most desired product, 1-hexene, shall be allowed. Depending on the nature of the co-catalyst and the reaction conditions, also the co-production of, e.g. 1-butene and 1-hexene, and 1-hexene and 1-octene, respectively, shall be provided.

The object is achieved by a catalyst composition comprising:
(a) a chromium compound;
(b) a ligand of the general structure
  (A) $R_1R_2P—N(R_3)—P(R_4)—N(R_5)—H$ or
  (B) $R_1R_2P—N(R_3)—P(R_4)—N(R_5)—PR_6R_7$
  wherein $R_1, R_2, R_3, R_4, R_5, R_6$ and $R_7$ are independently selected from halogen, amino, trimethylsilyl, $C_1$-$C_{10}$-alkyl, aryl and substituted aryl, or any cyclic derivatives of (A) and (B), wherein at least one of the P or N atoms of the PNPN-unit or PNPNP-unit is member of a ring system, the ring system being formed from one or more constituent compounds of structures (A) or (B) by substitution;
(c) an activator or co-catalyst.

As is to be understood, any cyclic derivatives of (A) and (B) can be utilized as ligand, wherein at least one of the P or N atoms of the PNPN-unit (structure (A)) or PNPNP-unit (structure (B)) is a ring member, the ring being formed from one or more constituent compounds of structures (A) or (B) by substitution, i.e. by formally eliminating per constituent compound either two whole groups $R_1$-$R_7$ (as defined) or H, one atom from each of two groups $R_1$-$R_7$ (as defined) or a whole group $R_1$-$R_7$ (as defined) or H and an atom from another group $R_1$-$R_7$ (as defined), and joining the formally so-created valence-unsaturated sites by one covalent bond per constituent compound to provide the same valence as initially present at a given site.

Suitable cyclic derivatives of (A) and (B) can be as follows:

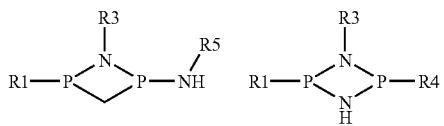

-continued

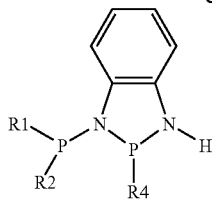

Preferably, the chromium compound is selected from organic or inorganic salts, coordination complexes and organometallic complexes of Cr(II) or Cr(III).

Most preferably, the chromium compound is selected from $CrCl_3(THF)_3$, Cr(III) acetylacetonate, Cr(III) octanoate, chromium hexacarbonyl, Cr(III)-2-ethylhexanoate and (benzene)tricarbonyl-chromium.

It is also preferred that $R_1, R_2, R_3, R_4, R_5, R_6$ and $R_7$ are selected from chloro, amino, trimethylsilyl, methyl, ethyl, isopropyl, tert-butyl, phenyl, benzyl, tolyl and xylyl.

Suitable ligands (A) and (B) having an amino-substituent can be as follows:

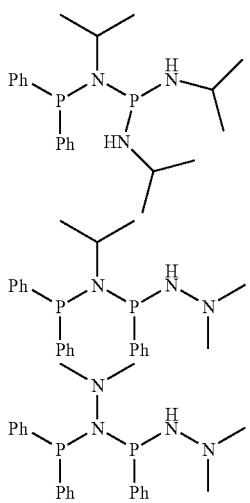

In one embodiment, the activator or co-catalyst is selected from trimethylaluminum, triethylaluminum, triisopropylaluminum, triisobutylaluminum, ethylaluminumsesquichloride, diethylaluminum chloride, ethylaluminumdichloride, methylaluminoxane (MAO) or mixtures thereof.

Most preferred, the ligand is selected from $(Ph)_2P—N(i-Pr)-P(Ph)-N(i-Pr)-H$, $(Ph)_2P—N(i-Pr)-P(Ph)-N(Ph)-H$, $(Ph)_2P—N(i-Pr)-P(Ph)-N(tert-butyl)-H$ and $(Ph)_2P—N(i-Pr)-P(Ph)-N(CH(CH_3)(Ph))-H$.

A catalyst composition is also preferably provided comprising a solvent.

Preferably, the solvent is selected from aromatic hydrocarbons, straight-chain and cyclic aliphatic hydrocarbons, straight-chain olefins and ethers, preferably toluene, benzene, ethylbenzene, cumene, xylenes, mesitylene, hexane, octane, cyclohexane, methylcyclohexane, hexene, heptene, octene, diethylether or tetrahydrofurane, most preferably toluene. Any mixture of these solvents may be used as well.

In one embodiment, the concentration of the chromium compound is from 0.01 to 100 mmol/l, preferably 0.1 to 10 mmol/l.

The ligand/Cr ratio is preferably from 0.5 to 50, preferably 0.8 to 2.0.

The Al/Cr ratio is preferably from 1 to 1000, preferably 10 to 200.

As is obvious for someone skilled in the art, the components (a) to (c) for providing the catalyst composition are more or less considered as starting materials, but may be converted when the three compounds (a)-(c) are mixed to form the catalyst composition. In this regard the catalyst composition according to the present invention can be also illustrated as being obtainable by combining at least:

(a) a chromium compound;
(b) a ligand of the general structure
  (A) $R_1R_2P\text{—}N(R_3)\text{—}P(R_4)\text{—}N(R_5)\text{—}H$ or
  (B) $R_1R_2P\text{—}N(R_3)\text{—}P(R_4)\text{—}N(R_5)\text{—}PR_6R_7$,
  wherein $R_1, R_2, R_3, R_4, R_5, R_6$ and $R_7$ are independently selected from halogen, amino, trimethylsilyl, $C_1$-$C_{10}$-alkyl, aryl and substituted aryl, or any cyclic derivatives of (A) and (B), wherein at least one of the P or N atoms of the PNPN-unit or PNPNP-unit is member of a ring system, the ring system being formed from one or more constituent compounds of structures (A) or (B) by substitution;
and
(c) an activator or co-catalyst.

According to the invention is also a process for di-, tri- and/or tetramerization of ethylene, comprising subjecting a catalyst composition of the invention to a gas phase of ethylene in a reactor and conducting an oligomerization.

Preferably, the oligomerization is carried out at a pressure of 1 to 200 bar, preferably 10 to 50 bar.

Also preferred, the oligomerization is carried out at a temperature of from 10 to 200° C., preferably 20 to 100° C.

In one embodiment, the process is carried out continuously, semi-continuously or discontinuously.

The mean residence time may be from 10 minutes to 20 hours, preferably 1 to 4 hours.

When combining the ligand according to general structure (A) and a co-catalyst, a reaction product can be obtained having the structural formula.

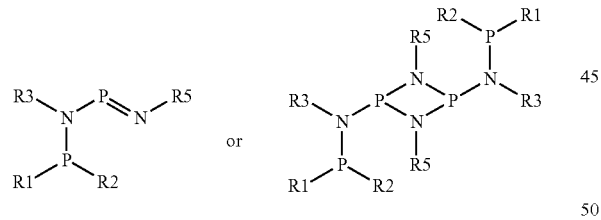

The reaction product disclosed above can, of course, be utilized in the catalyst composition instead of the separate addition of ligand and co-catalyst and shall be also within the scope of protection.

Under reaction conditions, the PNPN—H-type ligands are deprotonated in-situ by the cocatalyst. In a further advantageous embodiment of the present invention, the active catalyst species can be also formed ex-situ, by a separate deprotonation/elimination-step leading to the structures given above.

Especially, if smaller or sterically less demanding groups $R_1$-$R_7$ are used, the ligands tend to form dimers. These dimeric cyclodiphosphazanes can directly be used to form the active catalyst species.

The general ligand structures (A) and (B) as disclosed can be also illustrated by the following structural formula:

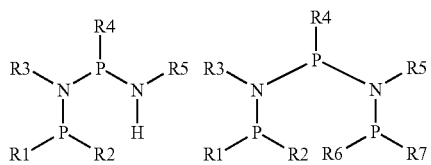

Most preferred ligand structures are $(Ph)_2P\text{—}N(i\text{-}Pr)\text{-}P(Ph)\text{-}N(i\text{-}Pr)\text{-}H$ and

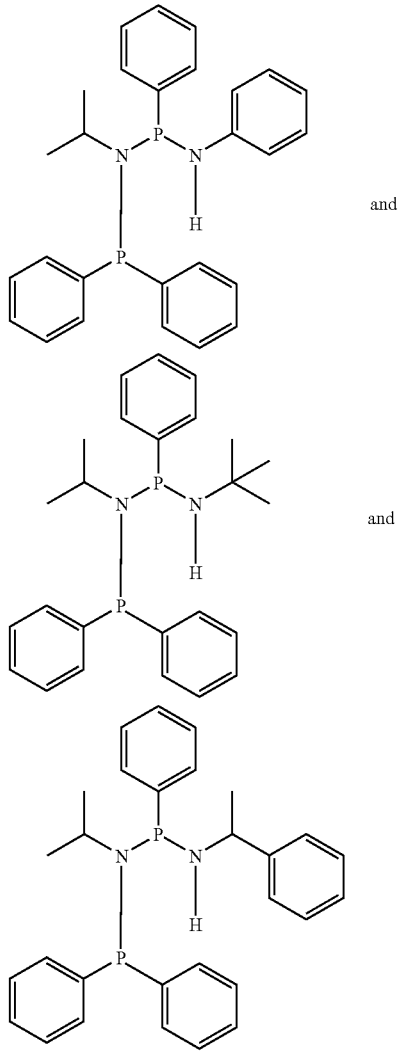

Surprisingly, it was found that with the inventive catalyst composition and the process for di-, tri- and tetramerization of ethylene the disadvantages of the prior art can be significantly overcome. Especially, the inventive process and the catalyst composition allows the production of 1-hexene with high turnover rate and selectivity. Further, high reproducibility is obtained, i.e. the catalyst composition is stable against interference from impurities and fluctuations in process conditions. Expensive co-catalysts, such as MAO, can be totally or to a large extent replaced by cheaper substances, preferably by triethylaluminium. Additionally, cocatalysts which are prone to quality instabilities, due to their relatively poor definition of chemical structure (e.g. MAO), are partly or totally replaced by well-defined chemical species (triethyl aluminium). With the inventive process no wide LAO product distribution is obtained, but specific alpha-olefins can be selectively produced. Further, the polymer formation is suppressed very well. Moreover, mild reaction conditions can be chosen, resulting consequently in low invest costs for technical-scale plant and low energy and operation costs. Additionally, a relatively simple, straight-forward process design is possible. Very high 1-hexene or 1-hexene/1-octene-selectivities lead to high product purities without additional purification steps in the separation train.

Further advantages and features of the present invention are now illustrated in the following examples section with reference to the accompanying drawing, wherein FIG. 1 is a GC/FID analysis of the liquid phase obtained in example 2.

The active catalyst may be prepared by combining the chromium source and the ligand in a suitable solvent, preferentially toluene, such that the chromium concentration is 0.01 to 100 mmol/l, preferentially between 0.1 and 10 mmol/l and the ligand/Cr-ratio is 0.5 to 50 mol/mol, preferentially between 0.8 and 2.0 mol/mol. The co-catalyst, preferentially triethylaluminum or any mixture of triethylaluminum and MAO or triethylaluminum and trimethylaluminum, is added as a solution in toluene, so as to result in an Al/Cr-ratio between 1 and 1000 mol/mol. The preferred Al/Cr-ratio is 10 to 200 mol/mol.

The solvent toluene can be replaced by other solvents such as aromatic hydrocarbons other than toluene (benzene, ethylbenzene, cumenene, xylenes, mesitylene etc.), aliphatic hydrocarbons (both straight-chain and cyclic, e.c hexane, octane, cyclohexane), straight-chain olefins like hexene, heptene, octene etc. or ethers like, for example diethylether or tetrahydrofurane.

The catalyst solution is then subjected to a gas phase of dry ethylene at pressures between 1 and 200 bar, preferentially 10 and 50 bar in a suitable pressure reactor. The reactor can be of any kind suitable to provide sufficient contact between gas- and liquid phase, such as bubble column reactors, stirred tank reactors, flow reactors with fixed or distributed ethylene-injection and the like.

Preferred reaction temperatures are between 10 and 200° C., the most preferred temperature regime is 20 to 100° C. Mean residence times and residence time distributions (in case of a continuous process) are chosen so as to achieve sufficient conversion at high selectivities. Typical mean residence times are between 10 minutes and 20 hours (depending on temperature and pressure). The preferred range is 1 to 4 hours.

EXAMPLE 1

Ligand Preparation 1.1 Preparation of Bis(isopropyl-amino)-phenylphosphine (NPN)

To a stirred solution of isopropylamine (30 ml, 352 mmol) in diethylether (250 ml), dichlorophenylphosphine (9.63 ml, 71 mmol, dissolved in 50 ml diethylether) was added at 0° C. over a period of 30 min. After stirring for a total of 72 hrs the solution was filtrated. The residue was washed with diethylether and the solvent was removed in vacuum. The remaining oil was distilled at 0.2 Torr/76-78° C. to give a colorless liquid with 33% yield (5.3 g). $^{31}P\{H\}$ NMR: 49.0 ppm.

1.2 Preparation of (phenyl)$_2$PN(isopropyl)P(phenyl)NH(isopropyl) (PNPN—H)

A solution of the NPN-species (as prepared in section 1.1)(2.4 g, 10.7 mmol) in tetrahydrofurane (10 ml) was added dropwise to a stirred solution of triethylamine (6 ml) and chlorodiphenylphosphine (2.36 g, 10.7 mmol) in thf (40 ml) at −40° C. After additional stirring for 24 h hrs at room temperature the triethylammonium salt was filtrated off and the residue was dissolved in n-hexane, filtrated again, and the solution was kept at −30° C. for crystallisation. Yield 52% (2.3 g, 5.6 mmol). $^{31}P\{H\}$ NMR: 41.2, 68.4 (broad).

EXAMPLE 2

Ethylene Trimerization

A 300 ml pressure reactor, equipped with dip tube, thermowell, gas entrainment stirrer, cooling coil, control units for temperature, pressure, and stirrer speed (all hooked up to a data acquisition system) was inertized with dry argon and filled with 100 ml anhydrous toluene. 1694 μl of a 4.017 wt %-solution of the ligand 1 ((phenyl)$_2$PN(isopropyl)P(phenyl) NH(isopropyl)) in toluene was combined with 59.2 mg CrCl$_3$ (thf)$_3$ (thf=tetrahydrofurane) under an argon blanket. This catalyst solution was transferred to the reactor under constant argon flow, along with 3.6 ml of a 1.9 mol/l solution of triethylaluminum in toluene.

The chosen volumes and masses correspond to a chromium concentration of 1 mmol/l at a ligand/CrCl$_3$(thf)$_3$ ratio of 1.5 mol/mol and a Al/Cr ratio of 70 mol/mol.

The reactor was sealed, pressurized with 30 bar dry ethylene and heated to 40° C. While stirring at 1200 rpm, the ethylene consumption was monitored by the data acquisition system and an electronic balance by constantly weighing the ethylene pressure cylinder. After 120 min residence time, the reaction in the liquid phase was quenched by transferring the liquid inventory by means of the ethylene pressure to a glass vessel filled with approx. 100 ml water. The entire gas phase from the reactor's head space was quantified by a calibrated gas meter and was then collected quantitatively in a purged and evacuated gas bag.

After separation of the liquid organic phase, the total mass was determined by weighing. Subsequently, the composition of the organic phase was analyzed by GC/FID. The previously collected gas phase was analyzed separately by GC/FID.

Based on the measured data, the mass balance was closed and the overall yields and selectivities were determined.

For illustration, a GC-trace of the liquid phase is given in FIG. 1. Surprisingly, a very high 1-hexene yield is observed, with only trace amounts of 1-butene, 1-octene, 1-decene and 1-dodecene. In repetitive experiments under clean and well-defined conditions, no discernible polymer formation was observed. The average C6-yield exceeds 89 wt % at 40° C. and degrades slightly with increasing temperature. Even more surprising than the high C6-yields are the 1-hexene selectivities within the C6-fraction. At 40° C. reaction temperature, the measured 1-hexene selectivities approach 100 wt %, i.e. are not distinguishable from 100 wt % within experimental error, thus rendering any polishing separation unit to ensure 1-hexene specifications obsolete in technical operations. The novel catalyst system disclosed in this invention is capable of suppressing very effectively any unwanted side reaction channel, such as olefin isomerization or -rearrangement, Friedel-Crafts-alkylation of the solvent, co-oligomerization and the like.

A summary of typical results from a series of non-optimized experiments is given in table 1. Higher temperatures, although causing deteriorating C6-yields, can, however, be useful for the co-production of C4- and C6-olefins, while still giving high 1-butene and 1-hexene selectivities (product purities) within the C4- and C6-fraction, respectively.

TABLE 1

Influence of temperature on C6-yields and 1-hexene selectivity (process parameters other than temperature as specified in example 1)

| Temperature C.° | C4-Yield, wt % | C6-Yield, wt % | 1-Hexene Selectivity in C6-Fraction, wt % |
|---|---|---|---|
| 40 | 8.2 | 89 | 100 |
| 65 | 9.6 | 84 | 97 |
| 90 | 33 | 52 | 90 |

Using different co-catalysts and/or by varying the structure of the functional groups of the ligand or the Cr/ligand-ratio, the system can be switched from a pure 1-hexene, i.e. ethylene-trimerization catalyst to a combined tri-/tetramerization system, producing 1-hexene and 1-octene with high selectivities.

With ligand 1, triethylaluminum as co-catalyst results in high 1-hexene yields, while MAO leads to 1-hexene and 1-octene.

Combinations of co-catalysts, such as triethylaluminum spiked with small amounts of MAO or trimethylaluminum, can increase the overall activity, i.e. the conversion rate, by a factor of at least three, while maintaining the high yields and selectivities.

Further preferred variations of the PNPN—H-structured basic ligand type were successfully synthesized and tested as shown above.

The features disclosed in the foregoing description, in the claims and in the drawing may, both separately and in any combination thereof, be material for realizing the invention in diverse forms thereof.

The invention claimed is:

1. A catalyst composition comprising:
   (a) a chromium compound;
   (b) a ligand of the general structure
      (A) $R_1R_2P$—$N(R_3)$—$P(R_4)$—$N(R_5)$—H,
      wherein $R_1$, $R_2$, $R_3$, $R_4$, and $R_5$ are independently selected from halogen, amino, trimethylsilyl, $C_1$-$C_{10}$-alkyl, aryl and substituted aryl, and said ligand may be a cyclic derivative of (A), wherein at least one of the P or N atoms of the ligand is a member of a ring system formed from one or more constituent compounds of the ligand by substitution;
      and
   (c) an activator or co-catalyst.

2. The catalyst composition according to claim 1, wherein the chromium compound is selected from organic or inorganic salts, coordination complexes and organometallic complexes of Cr(II) or Cr(III).

3. The catalyst composition according to claim 2, wherein the chromium compound is selected from $CrCl_3(THF)_3$, Cr(III)acetylacetonate, Cr(III)octanoate, chromium hexacarbonyl, Cr(III)-2-ethylhexanoate and (benzene)tricarbonylchromium.

4. The catalyst composition according to claim 2, wherein the ligand is selected from $(Ph)_2P$—N(i-Pr)-P(Ph)-N(i-Pr)-H, $(Ph)_2P$—N(i-Pr)-P(Ph)-N(Ph)-H, $(Ph)_2P$—N(i-Pr)-P(Ph)-N(tert-butyl)-H and $(Ph)_2P$—N(i-Pr)-P(Ph)-N(CH($CH_3$)(Ph))-H.

5. The catalyst composition according to claim 3, wherein $R_1$, $R_2$, $R_3$, $R_4$, and $R_5$ are selected from chloro, amino, trimethylsilyl, methyl, ethyl, isopropyl, tert-butyl, phenyl, benzyl, tolyl and xylyl.

6. The catalyst composition according to claim 5, wherein the activator or co-catalyst is selected from trimethylaluminum, triethylaluminum, triisopropylaluminum, triisobutylaluminum, ethylaluminumsesquichloride, diethylaluminum chloride, ethylaluminumdichloride, methylaluminoxane (MAO) or mixtures thereof.

7. The catalyst composition according to claim 5, wherein the chromium compound is selected from $CrCl_3(THF)_3$, Cr(III)acetylacetonate, Cr(III)octanoate, chromium hexacarbonyl, Cr(III)-2-ethylhexanoate and (benzene)tricarbonylchromium and the activator or co-catalyst is selected from trimethylaluminum, triethylaluminum, triisopropylaluminum, triisobutylaluminum, ethylaluminumsesquichloride, diethylaluminum chloride, ethylaluminumdichloride, methylaluminoxane (MAO) or mixtures thereof.

8. The catalyst composition according to claim 6, wherein the Al/Cr ratio is from 10:1 to 200:1.

9. A process for di-, tri- and/or tetramerization of ethylene, comprising contacting ethylene with the catalyst composition of claim 1 under ethylene oligomerization conditions.

10. The process according to claim 9, wherein said contacting is carried out at a pressure of 10 to 50 bar.

11. The process according to claim 10, wherein said contacting is carried out at a temperature of from 20° C. to 100° C.

12. The process according to claim 11, wherein the process is carried out continuously with a mean residence time of from 1 to 4 hours.

13. A catalyst composition comprising:
   (a) a chromium compound;
   (b) a ligand selected from $(Ph)_2P$—N(i-Pr)-P(Ph)-N(i-Pr)-H, $(Ph)_2P$—N(i-Pr)-P(Ph)-N(Ph)-H, $(Ph)_2P$—N(i-Pr)-P(Ph)-N(tert-butyl)-H and $(Ph)_2P$—N(i-Pr)-P(Ph)-N(CH($CH_3$)(Ph))-H; and
   (c) an activator or co-catalyst.

14. The catalyst composition according to claim 13, further comprising a solvent.

15. The catalyst composition according to claim 14, wherein the solvent is selected from toluene, benzene, ethylbenzene, cumene, xylenes, mesitylene, hexane, octane, cyclohexane, methylcyclohexane, hexene, heptene, octene, diethylether or tetrahydrofurane or mixtures thereof.

16. The catalyst composition according to claim 15, wherein the concentration of the chromium compound is from 0.1 to 10 mmol/l.

17. A process for di-, tri- and/or tetramerization of ethylene, comprising contacting ethylene with the catalyst composition of claim 15 under ethylene oligomerization conditions.

18. The catalyst composition according to claim 13, wherein the ligand/Cr ratio is 0.8 to 2.0.

19. A process for di-, tri- and/or tetramerization of ethylene, comprising contacting ethylene with the catalyst composition of claim 13 under ethylene oligomerization conditions.

20. A catalyst composition, obtained by combining at least:
   (a) a chromium compound;
   (b) a ligand of the general structure
      (A) $R_1R_2P$—$N(R_3)$—$P(R_4)$—$N(R_5)$—H,
      wherein $R_1$, $R_2$, $R_3$, $R_4$, and $R_5$ and are independently selected from halogen, amino, trimethylsilyl, $C_1$-$C_{10}$-alkyl, aryl and substituted aryl, and said ligand may be a cyclic derivative of (A), wherein at least one of the P or N atoms of the ligand is a member of a ring system formed from one or more constituent compounds of the ligand by substitution;
      and
   (c) an activator or co-catalyst.

* * * * *